United States Patent [19]

Lewis et al.

[11] Patent Number: 4,668,512
[45] Date of Patent: May 26, 1987

[54] PREPARATION OF PELLETS CONTAINING FUNGI AND NUTRIENT FOR CONTROL OF SOILBORNE PLANT PATHOGENS

[75] Inventors: Jack A. Lewis, Columbia; George C. Papavizas, Beltsville, both of Md.; William J. Connick, Jr., New Orleans, La.

[73] Assignee: The United States of America as represented by the Secretary of Agriculture, Washington, D.C.

[21] Appl. No.: 749,906

[22] Filed: Jun. 28, 1985

Related U.S. Application Data

[63] Continuation-in-part of Ser. No. 713,733, Mar. 20, 1985.

[51] Int. Cl.[4] ............................................. A01N 63/00
[52] U.S. Cl. ........................................................ 424/93
[58] Field of Search ........................................... 424/93

[56] References Cited

U.S. PATENT DOCUMENTS

| | | | |
|---|---|---|---|
| 2,441,729 | 5/1948 | Steiner | 426/271 |
| 3,649,239 | 3/1972 | Mitchell | 71/23 |
| 4,400,391 | 8/1983 | Connick | 424/304 |
| 4,401,456 | 8/1983 | Connick | 71/88 |

OTHER PUBLICATIONS

Doust, R. A., Journal of Invertebrate Pathology, 41:151–160 (1983).
TeBeest, D. O. and G. C. Templeton, 1985, Plant Dis., 69:6–10.
H. L., Walker and W. J. Connick, Jr., 1983, Weed Science, 31:333–338.
G. C. Papavizas, 1985, Annual Review of Phytopathology, 23:(in Press).
D. R. Fravel et al., 1985, Phytopathology, 75: (in Press).
Lewis, J. A. and Papavizas, G. C., Phytopathology, 24:(7) p. 836, Jul. 2, 1984.

*Primary Examiner*—Leonard Schenkman
*Assistant Examiner*—Joseph A. Lipovsky
*Attorney, Agent, or Firm*—M. Howard Silverstein; David G. McConnell; Raymond C. Von Bodungen

[57] ABSTRACT

This invention relates to a method for preparing pellets containing living biocontrol fungi and nutrient dispersed throughout. Living fungi are selected and grown for inoculum. The fungal propagules and wheat bran are added to a sodium alginate solution. The fungal propagule-alginate-bran mixture is added dropwise into a solution of calcium chloride. The resultant alginate gel pellets containing living fungi can be dried and used to inoculate agricultural fields infested with soilborne diseases.

14 Claims, No Drawings

PREPARATION OF PELLETS CONTAINING FUNGI AND NUTRIENT FOR CONTROL OF SOILBORNE PLANT PATHOGENS

CROSS REFERENCE TO RELATED APPLICATIONS

This is a continuation-in-part of Application Ser. No. 713,733, now pending filed Mar. 20, 1985.

BACKGROUND OF THE INVENTION (1) Field of the Invention

This invention relates to formulations of inoculum of microorganisms.

(2) Description of the Prior Art

New advances in biotechnology have focused on the production and delivery of bacterial and fungal biomass in formulations to be used as biological insecticides and herbicides (R. A. Doust, et al., 1983. Journal of Invertebrate Pathology 41:151-160; D. O. TeBeest and G. C. Templeton, 1985. Plant Disease 69:6-10; H. L. Walker and W. J. Connick, Jr., 1983. Weed Science 31:333-338). Similar technology with regard to production and delivery of biocontrol fungi effective against soilborne plant pathogens is almost nonexistent. The versatility, adaptability, and ease in handling species of fungi in the genera Trichoderma and Gliocladium has led to their effective use in biological control studies (G. C. Papavizas, 1985. Annual Review of Phytopathology 23: [Lin press]). However, the deficiencies in formulation technology are clearly an obstacle to the advancement of biological control research. Formulation of living, biocontrol propagules in alginate gel represents a breakthrough in biological control research. Recently, a procedure utilizing alginate gel formation to formulate spores of various biocontrol fungi and bacterial cells with a clay filler was described (D. R. Fravel, et al., 1985. Phytopathology 75:774-777).

Heretofore, various types of bulk organic matter, such as wheat bran, have been used to grow microorganisms. Non-granular formulations of fungi germinating on and colonizing bran have been applied loosely to soil to control certain plant diseases.

Connick, Jr., (U.S. Pat. Nos. 4,401,456 and 4,400,391) discloses processes for incorporating chemical, non-living, bioactive materials in alginate gels. Connick, Jr., (U.S. Pat. Nos. 4,401,456 and 4,400,391) discloses chemicals which are formulated to kill living matter. He also teaches the use of cations in the process, i. e. barium, copper, lead, zinc, all of which would be reasonably expected to kill any living fungi incorporated into the alginate gel.

The use of alginate gel technology to formulate agricultural products, pesticides and food items has also been disclosed. For example, U. S. Pat. No. 4,053,627 describes the use of alginate gel discs for mosquito control, U.S. Pat. No. 3,649,239 discloses fertilizer compositions, and U.S. Pat. No. 2,441,729 teaches the use of alginate gels as insecticidal as well as candy jellies. None of these patents discloses any method for incorporating living materials or fungi into an alginate gel matrix.

SUMMARY OF THE INVENTION

The formation of pellets containing living biocontrol fungi effective against selected soilborne plant pathogens using a food base and aqueous solutions of sodium alginate and calcium chloride ($CaCl_2$) is disclosed. The pelletized formulations of living fungi produced by this method have extended shelf life and are effective in allowing proliferation of the biocontrol fungi in soil, reducing inoculum density of the pathogen *Rhizoctonia solani* Kuehn, and preventing damping-off disease of cotton and sugar beet seedlings.

The method comprises the following steps in combination: selecting and growing a living fungi selected from the group consisting of: *Gliocladium virens* Gl-3, Gl-17 and Gl-21, *Trichoderma hamatum* TRI-4, Tm-23 and 31-3, *Trichoderma harzianum* Th-23-R9, WT-6-24 and Th-58, and Trichoderma viride T-1-R4, T-1-R9 and TS-1-R3 for sufficient time to be used as inoculum. The living fungal propagules are harvested, added to wheat bran and an aqueous solution of sodium alginate, of sufficient concentration to effect subsequent gelation. This mixture is homogenized and then added dropwise to an aqueous solution of calcium salt, thereby resulting in the formation of alginate gel beads containing living fungi and wheat bran nutrient dispersed throughout. The calcium salt can be either calcium chloride or calcium gluconate.

U. S. Pat. Nos. 4,401,456 and 4,400,391 teach a process for incorporating chemical bioactive materials in alginate gels. There is no teaching in said patents on, nor is there anticipated, the incorporation of living fungi as active materials. Indeed, one skilled in the art might expect fungi to die or become ineffective as a result of being incorporated in alginate pellets. The chemical bioactive materials of said U.S. Pat. Nos. 4,401,456 and 4,400,391 are released from the products by virtue of their water solubility (leaching or diffusion) or as a result of biodegradation of the alginate matrix. This is totally different from the growth and release of active propagules of a living fungus.

It was completely unexpected that a living fungus could be incorporated in alginate gel pellets or granules to give an effective material. For example, barium chloride and cupric chloride are among the prefered water-soluble metal salt gellants taught by U.S. Pat. Nos. 4,401,456 and 4,400,391 for use with chemical bioactive materials, but these salts are fungitoxic when used in the process of the present invention. Furthermore, the ability of the biocontrol fungi to survive the process of the present invention could not be predicted a priori because one would reasonably have expected the osmotic shock resulting from addition of the liquid alginate suspension into the calcium salt to kill the biocontrol fungi.

Other reasons why it is not obvious to use the teachings of U.S. Pat. Nos. 4,401,456 and 4,400,391 to produce effective fungus-containing pellets are stated below.

For biocontrol by fungi, the implicated mechanisms (competition, antibiosis, and parasitism) require an actively metabolizing antagonist. Consequently, the effectiveness of biocontrol fungi pelletized in an alginate matrix could not be expected since propagules of the fungi must grow free of the matrix to control pathogenic fungi. Also, one could not predict that the incorporation of ground wheat bran as a food base would provide enough nutrients to allow growth of the biocontrol fungi from the pellet into soil. In addition, it could not be anticipated that the bran would be of adequate bulk and density to allow formation of gelled pellets when the preparation is dropped into $CaCl_2$.

Stability of alginate gel pellets containing living fungi is very important for commerical reasons. The biocontrol fungi must survive for extended shelf life periods of time to meet shipping needs and agricultural uses.

Furthermore, other contaminant microorganisms are also pelletized along with the desired fungi during the formulation process. Since many microorganisms may be capable of competing with the desired fungi, the recovery and growth of the desired fungi after storage was impossible to predict beforehand. Applicants' biocontrol fungi-containing pellets produced living colonies of fungi when applied to an agricultural environment after extensive shelf life periods of time. This was totally unpredictable.

DESCRIPTION OF THE PREFERED EMBODIMENTS

The fungi used in the prefered embodiments of the invention have been identified as follows:

*Trichoderma viride* biotype T-1-R4 (NRRL No. 15955), (ATCC No. 52440).
*Trichoderma viride* biotype T-1-R9 (NRRL No. 15165), (ATCC No. 52442). (U.S. Pat. No. 4,489,161).
*Trichoderma viride* biotype TS-1-R3 (NRRL No. 15956).
*Trichoderma hamatum* isolate TRI-4 (NRRL No. 15949).
*Trichoderma hamatum* isolate Tm-23 (NRRL No. 15950).
*Trichoderma hamatum* isolate 31-3 (NRRL No. 15951).
*Trichoderma harzianum* biotype WT-6-24 (NRRL No. 15953).
*Trichoderma harzianum* biotype Th-23-R9 (NRRL No. 15952).
*Trichoderma harzianum* isolate Th-58 (NRRL No. 15954).
*Gliocladium virens* isolate Gl-3 (NRRL No. 15937).
*Gliocladium virens* isolate Gl-17 (NRRL No. 15947).
*Gliocladium virens* isolate Gl-21 (NRRL No. 15948).

All are on deposit with the Agricultural Research Culture Collection (NRRL) and available from: A. J. Lyons, Curator, ARS Patent Collection, Culture Collection Research, NRRC, 1815 N. University Street, Peoria, Ill. 61604. In addition, T-1-R4, T-1-R9, TRI-4, Th-58, Gl-3, Gl-17 have been deposited recently with the American Type Culture Collection, Rockville, Md. The T. viride T-L-R9 is a genetically manipulated biotype and has been patented (U.S. Pat. No. 4,489,161).

Each of the 12 fungi is cultured, processed, and pelletized separately to demonstrate the versatility of the procedure.

Cultures of fungi are maintained on V-8 juice agar (200 ml V-8 juice, 800 ml water, 1 g glucose, 20 g agar, 6.0 ml of 1.0 N NaOH) in light. Conidial suspensions for introduction into fermentation media are prepared from 9 to 12 day-old colonies. Fermentation (and seed) medium consists of water, blackstrap molasses (30 g/L) and brewer's yeast (5 g/L) and isused throughout. Fungi are first inoculated into 500-ml portions of seed medium in a container which is shaken on a rotary shaker for from about 3 to 7 days and from 20° to 26° C. Fifteen liters of fenmentation medium are placed in a vessel and autoclaved until sterile. This is inoculated by adding two liters of inoculum to the sterilized fermentation medium. The vessel is fitted with an attachable air vent through which filtered compressed air is allowed to enter and bubble through the broth to aerate and agitate the mixture. Applicants used a tube which exited the incoming filtered air near the bottom of the vessel for efficient aeration and agitation. The mixture was aerated and agitated with air for from about 5 to 15 days, at from about 20° to 26° C. Foam control can be accomplished by adding a sufficient amount of antifoam compound such as Antifoam A available from Sigma Chemical Co., St. Louis, Mo. 63178.

Solids from the fermentation medium are separated by filtration, such as through a cotton muslin filter. The resultant filter mats are weighed and can be used wet or dry. If dried, they are ground to a size adequate to process through pre-selected orifices.

For pellet formation 20 g of sodium alginate is dissolved in 750 ml of distilled water and autoclaved until sterile. A sufficient amount of wheat bran to provide adequate nutrient for propagule growth and proliferation of the biocontrol fungi is necessary. Therefore, concurrently 20 to 50 g of ground wheat bran is mixed with 250 ml water and autoclaved until sterile. Then, to a blender container, is added the alginate solution, wheat bran mixture and an amount of wet or dry biomass obtained by filtering 250 ml of fermentation medium previously inoculated with the preselected fungi. The resultant mixture is comminuted sufficiently to pass through the preselected orifices.

The mixture containing fungus, alginate, and bran is added dropwise through preselected orifices into gellant solution (2% $CaCl_2$, pH 5.4). Each droplet gels in the $CaCl_2$ solution and forms a distinct bead. Beads are separated from the solution such as by filtration, washed and dried at ambient temperature.

The simplicity of the requirements for carrying out the process of the present invention permits much latitude in equipment design. A suitable apparatus, described only for the purpose of illustration and not to be construed as limiting to the invention, consists of a reservoir to contain the alginate-propagule-bran mixture, a pump to feed this mixture, or a gravity-feed arrangement, from the reservoir to orifices which are from about 1–2 mm in diameter through which the mixture is added in a dropwise manner into a gellant solution contained in any convenient vessel. The alginate gel pellets that form have propagules of the selected fungus incorporated throughout and are harvested from the gellant solution by any suitable means. The alginate gel pellets may be dried to form dried pellets or granules making them suitable for storage and agricultural field use. A continuous process is possible involving the continuous removal of gel pellets and maintenance of an effective gellant solution concentration. It is also possible to extrude the alginate-propagule-bran mixture into the gellant solution to form a string-like gel which could be further processed to make granules. Sodium alginate is the preferred alginate because it is readily obtained commercially and does not have to be a high purity grade. Other water soluble salts of alginic acid such as potassium alginate may be used. Sodium alginate concentrations in the propagule-alginate-bran mixture can be 1.5–3% (w/v) but 2.0% is preferred because adequate gelling occurs at this level and concentrations of less than 1.5% tend to decompose during autoclaving.

A water soluble calcium salt such as $CaCl_2$ or calcium gluconate is necessary for gellation of sodium alginate solutions, and these compounds are not toxic to the fungi. An effective concentration range of $CaCl_2$, also called the salt or gellant solution, is 1–15% (w/v), but 2–3% is adequate and therefore preferred. Gelation proceeds faster as the concentration of the salt solution is increased.

It is preferred that the alginate solution be autoclaved before addition of the fungus biomass and that the bran-water mixture be autoclaved before addition to the alginate. This eliminates the possibility of rapid growth by contaminants found in natural alginate and natural bran, and enables the added biocontrol fungus to have an advantage in colonization of the pellets.

Biomass may be used wet or dry for pellet formulation. Dry biomass should be sufficiently ground to pass through the pre-selected orifices. It is not necessary to be concerned about particle size when wet biomass is used because comminution in the blender obviates the requirements for particles less than 425-mm in size.

Most desired fungi should be processed below 50° C., preferably in the range of 15° to 40° C. Dwell time of the gel pellets in the gellant solution can be from about 0.1 to 60 minutes, but 0.2 to 5 minutes is preferred.

The fungi reproduced when the gel pellets were placed in moist field soil or on appropriate microbiological media when brought into contact with moisture. Pellets produced as described above have sustained-release characteristics and provide residual activity to enhance the performance of the biocontrol fungi. Applicants' preferred embodiment also provides a useful method for storing inoculum for extended periods of time. Many of the antagonists enumerated above, when formulated as dried pellets, reproduced readily under field conditions when adequate moisture was present and effectively controlled targeted soilborne diseases (seed and seedling rots of plants) and pathogen (*Rhizoctonai solani*). Alginate formulations of biocontrol fungi and organic nutrient may be applied directly to soil as pellets. Formulation and production of alginate gel pellets containing the above-described living biocontrol fungi are readily illustrated in the following examples:

EXAMPLE 1

Cultures of *T. viride* T-1-R4 were maintained on V-8 juice agar as described supra. Conidial suspensions forintroduction into fermentation media were prepared from 9 to 12 day-old colonies. Fungi were first inoculated into 500ml portions of seed medium in a container which was shaken on a rotary shaker for 5 days at room temperature. Fifteen liters of fermentation medium (described supra) was placed in a carboy and autoclaved for 1 hour on two consecutive days. This was inoculated byadding two liters of inoculum to the 15 liters in the carboy to raise the total volume of the carboy to seventeen liters. A twenty-liter autoclavable polypropylene carboy with an 8-cm screw cap was used. A 3-cm hole was made close to the neck of the carboy and the hole was plugged with a rubber stopper which was perforated to allow air to flow into the medium through a tube that reached essentially to the bottom of the vessel. Filtered compressed air was allowed to bubble through the broth during the entire growth period for aeration and agitation of the broth for 5 to 15 days. Foam control was obtained by addition ofantifoam compound described supra. Solids from 250 ml of fermentation were separated by filtration through a cotton muslin filter fitted on a Buchner funnel. Although the resulting filter mat can be weighed and used wet or dry, the filter mat was airdried for three days, weighed and then ground in a Wiley mill to pass through a 40 mesh (425μm) screen.

For pellet formation, 20 g of sodium alginate was dissolved in 750 ml of distilled water at 40° C. while stirring, and then autoclaved. Concurrently, 50 g of wheat bran ground to pass a 425μm mesh screen was placed in a blender container with 250 ml of distilled water and then autoclaved. The ground filter mat material was then added to the blender container together with the alginate solution and the wheat bran-water mixture. The resultant wheat bran-alginate-fungal biomass mixture was comminuted for 30 sec at high speed and then added dropwise from a reservoir through tubes (each tube terminating in a 1 mm dia. orifice), the droplets falling a distance ofabout 15 cm into 200 ml of a 0.25 M $CaCl_2$gellant solution. Gel beads formed immediately upon contact with the gellant solution and were allowed to remain in the gellant solution for 20 minutes. The gel beads were separated by decanting, spread on a nylon screen, and dried at ambient temperature using a gentle flow of air. Drying transformed the gel beads into granules or pellets that weighed a total ofabout 75 g which were then stored under ambient conditions. Propagule (chlamydospore) numbers in pellets, number of colony-forming units in each gram of pellet after formation, and viability of the propagules after 1 and 24 weeks of storage at 5° and 25° C. were determined and reported in Table I. To calculate chlamydospore concentration, 1 g-portions of fermentor biomass were first comminuted in an ice bath with 100 ml water in a Tissumizer to detach chlamydospores from the mycelium. The chlamydospores were then separated from the mycelium using a series of nylon mesh fabrics of various pore sizes diluted with water, and counted with a hemacytometer. The number of chlamydospores in a unit of biomass and consequently in a pellet (number/g of pellet) was calculated.

Viability of the biomass incorporated into pellets was also determined. One gram of air-dried pellets was comminuted with 100 ml of water in a Tissumizer in an ice bath until the pellets were disintegrated. Serial dilutions of the homogenate were prepared and 1-ml aliquots were spread on TME medium (with or without benomyl). Fungal colonies were counted on the agar plates after 7–10 days of incubation at 25°–28° C. under continuous fluorescent light and populations were reported as colony-forming units (cfu)/g of pellet. Results in Table I show that there are $61.0\times10^6$ chlamydospore/g of T-1-R4 pellets which yield $6.9\times10^6$ cfu. After 1 week storage at 5° or 25° C. and 24 weeks storage at 5° or 25° C., viability of propagules in pellets is 80, 71, 60, and 10%, respectively.

EXAMPLE 2

Biomass of biotype T-1-R9 (*T. viride*) was grown, and pellets were formed, as described in Example 1. Results reported in Table I show that there were $82.1\times10^6$ chlamydospores/g of T-1-R9 pellets which yielded $7.3\times10^6$ cfu. After 1 week storage at 5° or 25° C. and 24 weeks storage at 5° or 25° C., viability of propagules in pellets was 72, 90, 80, and 5%, respectively.

EXAMPLE 3

Biomass of type of TS-1-R3 (*T. viride*) was grown, and pellets were formed, as described in Example 1. Results reported in Table I show that there were $68.8\times10^6$ chlamydospores/g of TS-1-R3 pellets which yielded $10.0\times10^6$ cfu. After 1 week storage at 5° or 25°

EXAMPLE 4

Biomass of biotype WT-6-24 (*T. harzianum*) was grown, and pellets were formed, as indicated in Example 1. Results reported in Table I show that there were $8.7 \times 10^6$ chlamydospores/g of WT-6-24 pellets which yielded $0.9 \times 10^6$ cfu. After 1 week storage at 5° or 25° C. and 24 weeks storage at 5° or 25° C., viability of propagules in pellets was 90, 86, 78, and 5%, respectively.

EXAMPLE 5

Biomass of biotype Th-23-R9 (*T. harzianum*) was grown, and pellets were formed, as described in Example 1. Results reported in Table I show that there were $173.2 \times 10^6$ cfu. After 1 week storage at 5° or 25° C. and 24 weeks storage at 5° or 25° C., viability of propagules in pellets was 107, 72, 23, and <5%, respectively.

EXAMPLE 6

Biomass of isolate Th-58 (*T. harzianum*) was grown, and pellets were formed, as described in Example 1. Results reported in Table I show that there were $128.0 \times 10^6$ chlamydospores/g of Th-58 pellets which yielded $10.4 \times 10^6$ cfu. After 1 week storage at 5° or 25° C. and 24 weeks storage at 5° or 25° C., viability of propagules in pellets is 77, 64, 64, and <5%, respectively.

EXAMPLE 7

Biomass of isolate TRI-4 (*T. hamatum*) was grown, and pellets were formed, as described in Example 1. Results reported in Table I show that there were $27.8 \times 10^6$ chlamydospores/g of TRI-4 pellets which yielded $3.9 \times 10^6$ cfu. After 1 week storage at 5° or 25° C. and 24 weeks storage at 5° or 25° C., viability of propagules in pellets was 71, 79, 80, and <5%, respectively.

EXAMPLE 8

Biomass of isolate Tm-23 (*T. hamatum*) was grown, and pellets were formed, as described in Example 1. Results reported in Table I show that there were $1.3 \times 10^6$ chlamydospores/g of Tm-23 pellets which yielded $0.2 \times 10^6$ cfu. After 1 week storage at 5° or 25° C. and 24 weeks storage at 5° or 25° C., viability of propagules in pellets was 60, 40, 5, and 5%, respectively.

EXAMPLE 9

Biomass of isolate 31-3 (*T. hamatum*) was grown, and pellets were formed, as described in Example 1. Results reported in Table I show that there were $15.9 \times 10^6$ chlamydospores/g of 31-3 pellets which yielded $2.0 \times 10^6$ cfu. After 1 week storage at 5° or 25° C. and 24 weeks storage at 5° or 25° C., viability of propagules in pellets was 73, 51, 5, and <5%, respectively.

EXAMPLE 10

Biomass of isolate Gl-3 (*G. virens*) was grown, and pellets were formed, as described in Example 1. Results in Table I show that there were $114.0 \times 10^6$ chlamydospores/g of Gl-3 pellets which yielded $6.3 \times 10^6$ cfu. After 1 week storage at 5° or 25° C. and 24 weeks storage at 5° or 25° C., viability of propagules in pellets was 86, 84, 94, and <5%, respectively.

EXAMPLE 11

Biomass of isolate Gl-17 (*G. virens*) was grown, and pellets were formed, as described in Example 1. Results reported in Table I show that there were $117.8 \times 10^6$ chlamydospores/g of Gl-17 pellets which yielded $6.9 \times 10^6$ cfu. After 1 week storage at 5° or 25° C. and 24 weeks storage at 5° or 25° C., viability of propagules in pellets was 93, 93, 86and <5%, respectively.

EXAMPLE 12

Biomass of isolate Gl-21 (*G. virens*) was grown, and pellets were formed, as described in Example 1. Results reported in Table I show that there were $121.0 \times 10^6$ chlamydospores/g of Gl-17 pellets which yielded $6.6 \times 10^6$ cfu. After 1 week storage at 5° or 25° C. and 24 weeks storage at 5° or 25° C., viability of propagules in pellets was 90, 90, 90, and <5%, respectively.

EXAMPLE 13

Pellets of TRI-4 (*T. hamatum*), prepared as in Example 1, were added at a rate of 0.5% by wt to soil containing beet seed infested with the pathogen, *R. solani*. The effect of pellets on survival was determined. Soils were moistened to about −0.3 bars and maintained at 21°–23° C. in beakers covered with polyethylene film punctured to penmit gas exchange. After 1, 2, 3, and 6 week incubation, beet seed were retrieved from 150 g of soil on a sieve (1.4 -mm mesh), washed, and 10 seed plated on 2% water agar with antibiotics. The characteristic, branched growth of Rs was detected as described previously on plates after 20–24 hr of incubation at 23°–25° C. Survival was expressed as the percentage of beet seed that remained colonized by Rs. The effect of pellets on damping-off disease of cotton and sugar beet in *R. solani*-infested soil was also detenmined. Soils were placed in plastic flats ($18 \times 12 \times 6.5$ cm), incubated for 1 wk, and planted with thiram-treated seed of cotton and sugar beet. The flats, planted with two rows each of 10 seed, were maintained in the greenhouse at 21°–23° C., watered and supplemented with 12 hr photoperiod of 16,000 lux when necessary. Plant stands were counted 1, 2,and 3 wk after planting and Rs inoculum in soil was assayed at 3 wk with the beet seed colonization method. The experiments were repeated twice with five replications.

Pellets with TRI-4 reduced survival of *R. solani* 78%. There was no cotton or sugar beet stand in pathogen-infested soil; with pellets, stands of cotton and sugar beet were 110 and 78% of the stands in noninfested control soils, respectively.

EXAMPLE 14

Pellets of TS-1-R3 (*T. viride*) were prepared as in Example 1 and pathogen survival and disease reduction assayed as in Example 13. Pellets with TS-1-R3 reduced survival of *R. solani* 50%. There was no cotton or sugar beet stand in pathogen-infested soil; with pellets, stands of cotton and sugar beet were 45 and 44% of the stands in noninfested control soil, respectively.

EXAMPLE 15

Pellets of Gl-21 (*G. virens*) were prepared as in Example 1 and pathogen survival and disease reduction assayed as in Example 13. Pellets with Gl-21 reduced survival of *R. solani* 70%. There was no cotton or sugar beet stand in pathogen-infested soil; with pellets, stands of cotton and sugar beet were 95 and 58% of the stands is noninfested control soils, respectively.

EXAMPLE 16

Pellets of T-1-R9 (*T. viride*) were prepared as in Example 1 and pathogen survival assayed as in Example 13. Pellets with T-1-R9 reduced survival of *R. solani* 8%.

EXAMPLE 17

Pellets of WT-6-24, Th-58, and Th-23-R9 (*T. harzianum*) were prepared as in Example 1 and pathogen survival assayed as in Example 13. Pellets of WT-6-24, Th-58, and Th-23-R9 reduced survival of *R. solani* 14, 80, and 56%, respectively.

EXAMPLE 18

Pellets of Tm-23 and 31-3 (*T. hamatum*) were prepared as in Example 1 and pathogen survival assayed as in Example 13. Pellets of Tm-23 and 31-3 reduced survival of *R. solani* 38 and 64%, respectively.

EXAMPLE 19

Pellets of Gl-3 and Gl-17 (*G. virens*) were prepared as in Example 1 and pathogen survival assayed as in Example 13. Pellets of Gl-3 and Gl-17 reduced survival of *R. solani* 23 and 46%, respectively.

EXAMPLE 20

Pellets of TRI-4 (*T. hamatum*) were prepared as in Example 1 using 0.95, 1.9, 3.75, and 7.5 g dry biomass per liter of formulation and pathogen survival assayed as in Example 13. After 1 week of incubation, pellets of TRI-4 with 0.95, 1.9, 3.75 and 7.5 g dry biomass per liter of formulation reduced survival of *R. solani* 22, 88, 94, and 84%, respectively. Therefore, small quantities of dry biomass in pellet formation are effective in reducing survival of the pathogen *R. solani* in soil.

EXAMPLE 21

Pellets of Th-58 (*T. harzianum*) were prepared as in Example 1 and stored for 3 to 12 weeks at 5° and 25° C. Pathogen survival was assayed as in Example 13, 3 weeks after pellets were added to soil. Pellets of Th-58 for 3 weeks at 5° and 25° C. reduced survival of *R. solani* 69 and 78%, respectively. Pellets of Th-58 stored for 12 weeks at 5° and 25° C. reduced survival of *R. solani* 36, and 27%, respectively, thereby demonstrating good stability during storage.

EXAMPLE 22

Pellets of TRI-4 (*T. hamatum*) were prepared as in Example 1 and stored for 3 and 12 weeks at 5° and 25° C. Pathogen survival was assayed as in Example 13, 3 weeks after pellets were added to soil. Pellets of TRI-4 stored for 3 weeks at 5° and 25° C. reduced survival of *R. solani* 62 and 76%, respectively. Pellets of TRI-4 stored for 12 weeks at 5° and 25° C. reduced survival of *R. solani* 26 and 5%, respectively, thus showing stability during storage.

TABLE I

Biological Characteristics of Alginate Pellets Formed from Bran and Fermentor Biomass of Various Isolates of Trichoderma spp. and *Gliocladium virens*

| Species and Isolate | Chlamydospores ($\times 10^6$/g pellet)[a] | Colony-forming units ($\times 10^6$/g pellet)[b] | Viability (%)[c] at indicated Storage Time and Temperature | | | |
|---|---|---|---|---|---|---|
| | | | 1 wk | | 24 wk | |
| | | | 5° C. | 25° C. | 5° C. | 25° C. |
| *T. viride* | | | | | | |
| T-1-R4 | 61.1 | 6.9 | 80 | 71 | 60 | 10 |
| T-1-R9 | 82.1 | 7.3 | 72 | 90 | 80 | <5 |
| TS-1-R3 | 68.8 | 10.0 | 92 | 105 | 85 | 10 |
| *T. harzianum* | | | | | | |
| WT-6-24 | 8.7 | 0.9 | 90 | 86 | 78 | <5 |
| Th-23-R9 | 173.2 | 11.1 | 107 | 72 | 23 | <5 |
| Th-58 | 128.0 | 10.4 | 77 | 64 | 64 | <5 |
| *T. hamatum* | | | | | | |
| TRI-4 | 27.8 | 3.9 | 71 | 79 | 80 | <5 |
| Tm-23 | 1.3 | 0.2 | 60 | 40 | <5 | <5 |
| 31-3 | 15.9 | 2.0 | 73 | 51 | <5 | <5 |
| *G. virens* | | | | | | |
| Gl-3 | 114.0 | 6.3 | 86 | 84 | 94 | <5 |
| Gl-17 | 117.8 | 6.9 | 93 | 93 | 86 | <5 |
| Gl-21 | 121.0 | 6.6 | 90 | 90 | 90 | <5 |

[a]Chlamydospore numbers assayed in fermentor biomass immediately before pellet formation. Numbers counted with hemacytometer.
[b]Colony-forming units in pellets at time of formation determined on Trichoderma medium E.
[c]Viability is expressed as percentage of control which is the colony-forming units/g of pellet assayed at time of formation of air-dried pellets.

We claim:

1. A method for producing pellets containing living fungi and wheat bran nutrient for the control of soil-borne diseases comprising:

(a) growing living fungi selected from the group consisting of *Gliocladium virens* Gl-3, Gl-17 and Gl-21, *Trichoderma hamatum* TRI-4, Tm-23 and 31-3, *Trichoderma harzianum* Th-23-R9 and WT-6-24 and Th-58, and *Trichoderma viride* T-1-R4, T-1-R9 and T-1-R3 for sufficient time to produce an effective amount of living chlamydospores for control of soil borne plant disease caused by *Rhizoctonia solani*;

(b) harvesting the living chlamydospores of (a);

(c) adding the chlamydospores and wheat bran to an aqueous solution of sodium alginate of sufficient concentration to effect subsequent gelation;

(d) homogenizing the mixture of (c) and then adding dropwise the homogenized mixture to an aqueous solution of calcium salt, said calcium salt selected from the group consisting of calcium chloride and calcium gluconate, thereby forming alginate gel beads containing living chlamydospores of fungi and wheat bran nutrient dispersed throughout;

(e) drying the alginate gel beads of (d).

2. The method of claim 1 wherein the chlamydospores are harvested by filtration, thus resulting in a wet mat biomass of chlamydospores.

3. The claim 2 including drying the alginate gel beads containing the living chlamydospores and the wheat bran nutrient dispersed through out thereby transforming the gel beads into granules or pellets.

4. The method of claim 3 including drying the wet filter biomass mat and then grinding the dried biomass to a size sufficient to pass through pre-selected orifices.

5. Alginate gel pellets containing living chlamydospores and wheat bran nutrient dispersed throughout, said pellets produced in accordance with the process of claim 4.

6. The method of claim 1 wherein the wheat bran and aqueous sodium alginate solution are separately autoclaved for sufficient time to insure sterility prior to the addition of the living chlamydospores.

7. The method of claim 1 wherein the sodium alginate concentration is from about 2 to 3% (w/v) in water.

8. The method of claim 1 wherein the calcium chloride concentration is from about 2 to 3% by weight in water.

9. The method of claim 1 wherein the concentration of wheat bran is from about 2 to 5% (w/v).

10. Alginate gel pellets containing living chlamydospores and wheat bran nutrient dispersed throughout said pellets produced in accordance with the process of claim 1.

11. Alginate gel pellets comprising an alginate gel matrix dispersed throughout with effective concentrations of living chlamydospores of fungi which are effective for control of soilborne plant disease caused by *Rhizoctonia solani* as the active ingredient and a sufficient amount of wheat bran to provide nutrient for growth and proliferation of the fungus.

12. The alginate gel pellets of claim 11 wherein the living chlamydospores are produced from fungi selected from the group consisting of: *Gliocladium virens* Gl-3, Gl-17 and Gl-21, *Trichoderma hamatum* TRI-4, Tm-23 and 31-3, *Trichoderma harzianum* Th-23-R9, WT-6-24 and Th-58, and *Trichoderma viride* T-1-R9 and TS-1-R3.

13. Dried alginate gle pellets of claim 12.

14. A method for controlling soilborne plant diseases in an agricultural field comprising:

(a) growing a living fungus selected from the group consisting of *Gliocladium virens* Gl-3, Gl-3, Gl-17 and Gl-21, *Trichoderma hamatum* TRI-4, Tm-23 and 31-3, *Trichoderma harzianum* Th-23-R9, Wt-6-24 and Th-58, and *Trichoderma viride* T-1-R4, T-1-R9 and TS-1-R3 for sufficient time to produce an effective amount of living chlamydospores for control of soilborne plant disease caused by *Rhizoctonia solani;*

(b) harvesting the living chlamydospores of (a);

(c) adding the living chlamydospores and wheat bran to an aqueous solution of sodium alginate, of sufficient concentration to effect subsequent gelation;

(d) homogenizing the mixture of (c) and then adding dropwise the homogenized mixture to an aqueous solution of a calcium salt, said calcium salt selected from the group consisting of calcium chloride and calcium gluconate, thereby forming alginate gel beads containing living chlamydospores of fungi and wheat bran nutrient disperse throughout;

(e) drying the gel beads of (d) thereby transforming the gel beads into granules or pellets;

(f) applying the pellets of (e) to an agricultural field infested with soilborne plant disease caused by *Rhizoctonia solani* wherein the living fungi reproduce and control said soilborne plant disease caused by said *Rhizoctonia solani.*

* * * * *